(12) United States Patent
Strola et al.

(10) Patent No.: US 9,739,716 B2
(45) Date of Patent: Aug. 22, 2017

(54) METHOD FOR REGULATING THE RELATIVE POSITION OF AN ANALYTE IN RELATION TO A LIGHT BEAM

(71) Applicant: Commissariat a l'energie atomique et aux energies alternatives, Paris (FR)

(72) Inventors: Samy Strola, Grenoble (FR); Cedric Allier, Grenoble (FR); Mathieu Dupoy, Grenoble (FR); Emmanuelle Schultz, Saint Egreve (FR)

(73) Assignee: COMMISSARIAT À L'ÉNERGIE ATOMIQUE ET AUX ÉNERGIES ALTERNATIVES, Paris (FR)

( * ) Notice: Subject to any disclaimer, the term of this patent is extended or adjusted under 35 U.S.C. 154(b) by 0 days.

(21) Appl. No.: 14/764,185

(22) PCT Filed: Jan. 30, 2014

(86) PCT No.: PCT/EP2014/051775
§ 371 (c)(1),
(2) Date: Jul. 29, 2015

(87) PCT Pub. No.: WO2014/118263
PCT Pub. Date: Aug. 7, 2014

(65) Prior Publication Data
US 2016/0011117 A1 Jan. 14, 2016

(30) Foreign Application Priority Data
Jan. 31, 2013 (FR) ..................... 13 50857

(51) Int. Cl.
*G01B 11/02* (2006.01)
*G01N 21/00* (2006.01)
(Continued)

(52) U.S. Cl.
CPC ............. *G01N 21/65* (2013.01); *G01N 21/01* (2013.01); *G01N 21/13* (2013.01);
(Continued)

(58) Field of Classification Search
CPC ..... G01N 2021/135; G01N 2001/4027; G01N 21/4788; G01N 21/65; G01N 21/13;
(Continued)

(56) References Cited

U.S. PATENT DOCUMENTS 6,067,463 A * 5/2000 Jeng ..................... A61B 5/1455
600/310
6,407,812 B1 * 6/2002 Kurozumi ............ G02B 7/1827
356/336

(Continued)

OTHER PUBLICATIONS

"Microtechnologies for Biology and Healthcare", Leti Annual Research Report 2012, XP002698908.
(Continued)

*Primary Examiner* — Sunghee Y Gray
(74) *Attorney, Agent, or Firm* — Young & Thompson

(57) ABSTRACT

A method for regulating the relative position of an analyte of a sample (16) in relation to a light beam (F) includes the illumination of the analyte of the sample (16) with the light beam (F), capturing by an imaging device (38) a transmission image of the beams scattered by the analyte of the sample (16) in order to establish a diffraction pattern, and modifying the relative position of the analyte of the sample (16) in relation to the light beam (F) according to at least one property of the diffraction pattern.

11 Claims, 8 Drawing Sheets

(51) Int. Cl.
*G01N 33/00* (2006.01)
*G01N 21/65* (2006.01)
*G01N 21/01* (2006.01)
*G01N 21/13* (2006.01)
*G03H 1/04* (2006.01)

(52) U.S. Cl.
CPC ..... *G03H 1/0443* (2013.01); *G01N 2021/135* (2013.01); *G03H 2001/045* (2013.01); *G03H 2001/0447* (2013.01)

(58) Field of Classification Search
CPC ...... G01N 21/45; G01N 21/41; G01N 21/645; G01N 33/582; G01N 33/48; G01N 33/80; G01N 33/4905; G01N 2015/1006; G01N 2015/1454; G01N 2015/1481; G01N 2015/0073; G01N 2015/1075; G01N 15/1434; G01N 15/1475; G01N 15/1436; G01B 9/02041
USPC ......... 356/521, 338, 36, 445, 432–440, 244, 356/246; 435/7.25, 29, 288.7
See application file for complete search history.

(56) References Cited

U.S. PATENT DOCUMENTS

| | | | | |
|---|---|---|---|---|
| 8,994,940 B2* | 3/2015 | Dowaki | ............. | G01N 21/4785 356/243.2 |
| 2007/0195333 A1* | 8/2007 | Negishi | ................. | B82Y 35/00 356/601 |
| 2011/0136165 A1* | 6/2011 | Vojnovic | ............ | G01N 15/1456 435/39 |

OTHER PUBLICATIONS

C.P. Alliet et al.: "Bacteria detection with thin wetting film lensless imaging", Biomed. Opt. Express, vol. 1, No. 3, Oct. 1, 2010, pp. 762-770, XP055066537.

European Official Action issued in Application Serial No. EP14702013.5, dated Sep. 30, 2016.

Podbielska, H. et al., "Bacterial Classification by Means of the Statistical Analysis of Fresnel Diffraction Patterns of Bacterial Colonies," Biomedical Optics and 3D Imaging Postdeadline, 2012, pp. 1-3.

Buzalewicz, I. et al., "Diffraction Signature of Bacteria Colonies and the Influence of Different Incubation conditions," FIO/LS Technical Digest, 2011, pp. 1-2.

Buzalewicz, I. et al., "Influence of Various Growth Conditions on Fresnel Diffraction Patterns of Bacteria Colonies Examined in the Optical System with Converging Spherical Wave Illumination," Optics Express, vol. 19, No. 22, Oct. 24, 2001, pp. 1-18.

Suchwalko, A. et al., "Computer-Based Classification of Bacteria Species by Analysis of their Colonies Fresnel Diffraction Patters," Proc. of SPIE, vol. 8212, 2012, pp. 82120R-1-82120R-13.

Alon Greenbaum and Ayodogan Ozcan: "Maskless imaging of dense samples using pixel super-resolution based multi-height lensfree on-chip microscopy", Optics Express, vol. 20, No. 3, Jan. 30, 2012 (Jan. 30, 2012), pp. 3129-3143, XP055066626.

"Microtechnologies for Biology and Healthcare", Leti Annual Research Report 2012, XP002698908, retrieved on Jun. 18, 2013.

C.P. Alliet et al.: "Bacteria detection with thin welling film lensless imaging", Biomed. Opt. Express, vol. 1, No. 3, Oct. 1, 2010, pp. 762-770, XP055066537.

International Search Report PCT/EP2014/051775 dated Apr. 4, 2014.

* cited by examiner

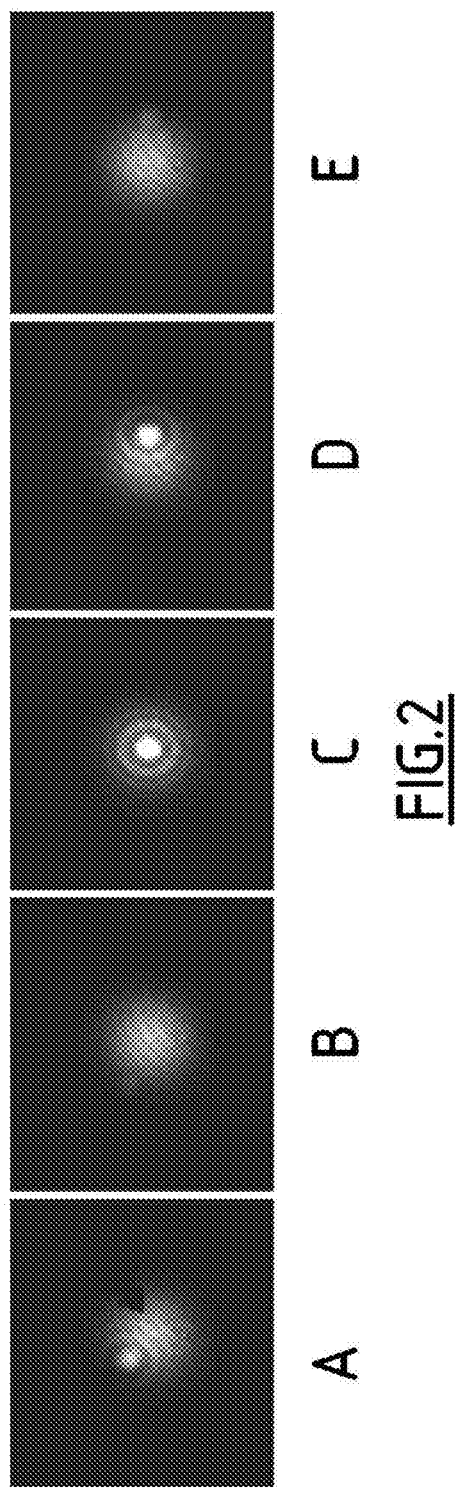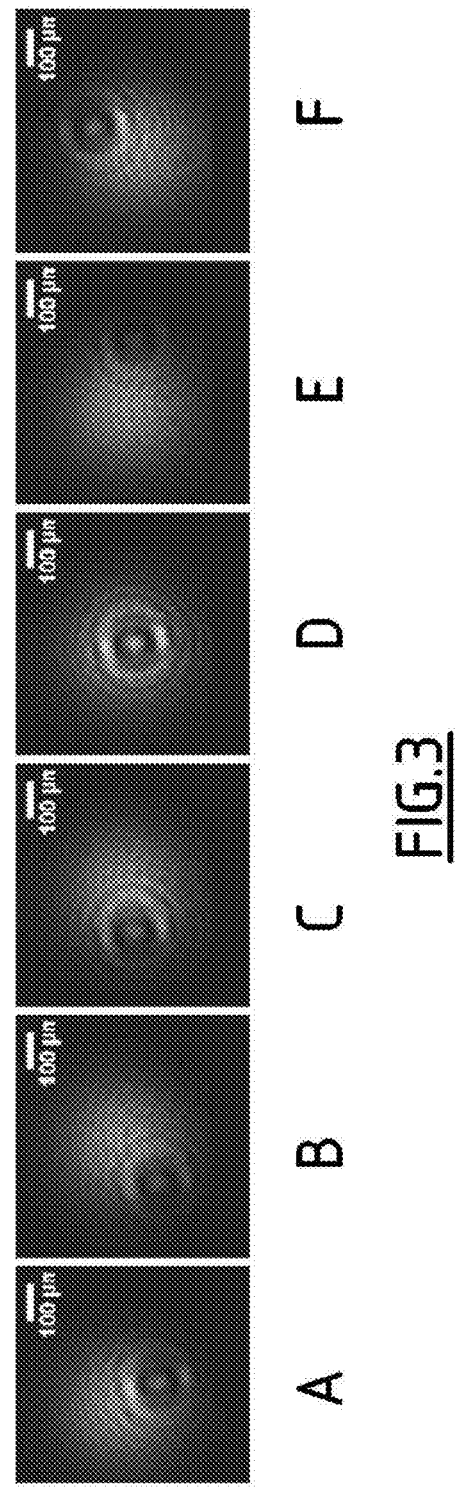
FIG.2
FIG.3

_(10)_ METHOD FOR REGULATING THE RELATIVE POSITION OF AN ANALYTE IN RELATION TO A LIGHT BEAM

BACKGROUND OF THE INVENTION

The present invention relates to a method for regulating the relative position of an analyte of a sample in relation to a light beam. The present invention also relates to a method for analyzing an analyte of a sample by means of a light beam. The present invention also relates to the associated sample holder and optical system.

DESCRIPTION OF THE RELATED ART

In the field of spectrometric analysis, an analysis device comprising an optical probe is used. The optical probe allows excitation of an analyte, which allows a signal to be collected stemming from the analyte as a response to the excitation of the probe. The quality of the signal and therefore of the analysis implies alignment of the optical probe on the analyte as accurately as possible. This is delicate when the dimensions of the analyte are small, for example of the order of one micrometer.

In order to produce the alignment, a system including an analysis device with an optical probe combined with a microscope architecture is known from document US-A-2012/0040330. The system is adapted so as to operate in an imaging mode in which the analyte is illuminated by a white light beam and in an analysis mode in which the analyte is illuminated by the optical probe. The alignment on the analyte is ensured with the white light beam and by using objectives with increasing magnification of the microscope architecture.

But, this system imposes a relatively long alignment time. Further the alignment is only guaranteed if the position of the beam from the optical probe is identical both in the imaging mode and in the analysis mode. This requires regular verification of the position of the beam from the optical probe in order to prevent any lack of alignment.

Therefore, there exists a need for a method for regulating the relative position of an analyte in relation with a light beam, which is faster.

SUMMARY OF THE INVENTION

According to the invention, this object is achieved by a method for regulating the relative position of an analyte of a sample in relation to a light beam. The method comprises the illumination of the analyte of the sample with the light beam, the taking by the imaging device of an image in transmission of the beams scattered by the analyte of the sample in order to establish a diffraction pattern, and the modification of the relative position of the analyte of the sample with respect to the light beam according to at least one property of the diffraction pattern.

According to particular embodiments, the regulation method comprises one or several of the following characteristics, taken individually or according to any technically possible combination:

the light beam stems from a light source and propagates along a propagation axis.

the modification of the position of the analyte of the sample with respect to the light beam comprises at least one of the following steps:

aligning the analyte of the sample on the propagation axis of the light beam, modifying the distance between the light source and the analyte of the sample along the propagation axis so that the diffraction pattern resulting from the beams scattered by the analyte of the sample is at the centre of the diffraction pattern, adjusting the distance between the light source and the analyte of the sample along the propagation axis until the analyte of the sample occults the light beam, and modifying the relative position of the analyte of the sample in relation to the beam in order to maximize the radiation emitted by the analyte of the sample in response to the excitation from the light beam.

each step is applied depending on a property of the diffraction pattern, the property being different for each of the steps.

the taking by an imaging device of an image in transmission of the beams scattered by the analyte of the sample in order to establish a diffraction pattern and the modification of the relative position of the analyte of the sample in relation to the light beam depending on at least one property of the diffraction pattern are carried out several times.

the property is the morphology of the diffraction pattern or the position of the diffraction pattern with respect to the spot formed by the light beam in the transmission image.

the method further comprises the acquisition of an analysis signal resulting from the radiation emitted by the analyte of the sample in response to the illumination with the light beam by an analysis device, and modification of the relative position of the analyte of the sample with respect to the beam in order to optimize at least one characteristic of the acquired analysis signal.

the imaging device is an imaging device without any lenses.

The invention also relates to a method for analyzing an analyte of a sample by means of a light beam. The method comprises the regulation of the relative position of the analyte of the sample in relation to the light beam by applying a regulation method as described earlier and the analysis by an analysis device of the radiation emitted by the analyte of the sample in response to the illumination with the light beam.

According to particular embodiments, the regulation method comprises one or more of the following features, taken individually or according to any technically possible combination:

the method successively comprises the attenuation of the light beam with an attenuation means, the regulation of the relative position of the analyte of the sample in relation to light beam, the stopping of the attenuation of the light beam and the analysis by the analysis device.

the method further comprises the determination of characteristics of the analyte of the sample from the diffraction pattern established by the imaging device.

The invention also relates to a sample holder able to hold a sample comprising at least one analyte. The sample holder comprises an imaging device capable of taking a transmission image of the beams scattered by an analyte of the sample in order to establish a diffraction pattern, and a unit for regulating the relative position of the analyte or sample in relation to a light beam capable of modifying the relative position of the analyte of the sample according to at least one property of the diffraction pattern.

According to a particular embodiment, the imaging device is an imaging device without lenses.

The invention also relates to an optical system including a light source able to illuminate an analyte of the sample with a light beam, and the sample holder as described earlier.

According to particular embodiments, the optical system comprises one or several of the following features, taken individually or according to any technically possible combination:
- the regulation unit comprises a means for translating the light source along the propagation direction of the light beam and a means for displacing the sample holder in the plane perpendicular to the propagation direction of the light beam.
- an assembly including the light source and an analysis device, the means for translating the light source being able to displace the assembly along the direction of propagation of the light beam.

BRIEF DESCRIPTION OF THE DRAWING FIGURES

Other features and advantages of the invention will become apparent upon reading the description which follows of embodiments of the invention, given only as an example and with reference to the drawings wherein:

FIGS. 2A to 2E are diffraction patterns observed during a first embodiment of a step of an alignment method according to the invention;

FIGS. 3A to 3F are diffraction patterns observed during a second embodiment of a step of an alignment method according to the invention;

DETAILED DESCRIPTION OF THE INVENTION

Figure 1:
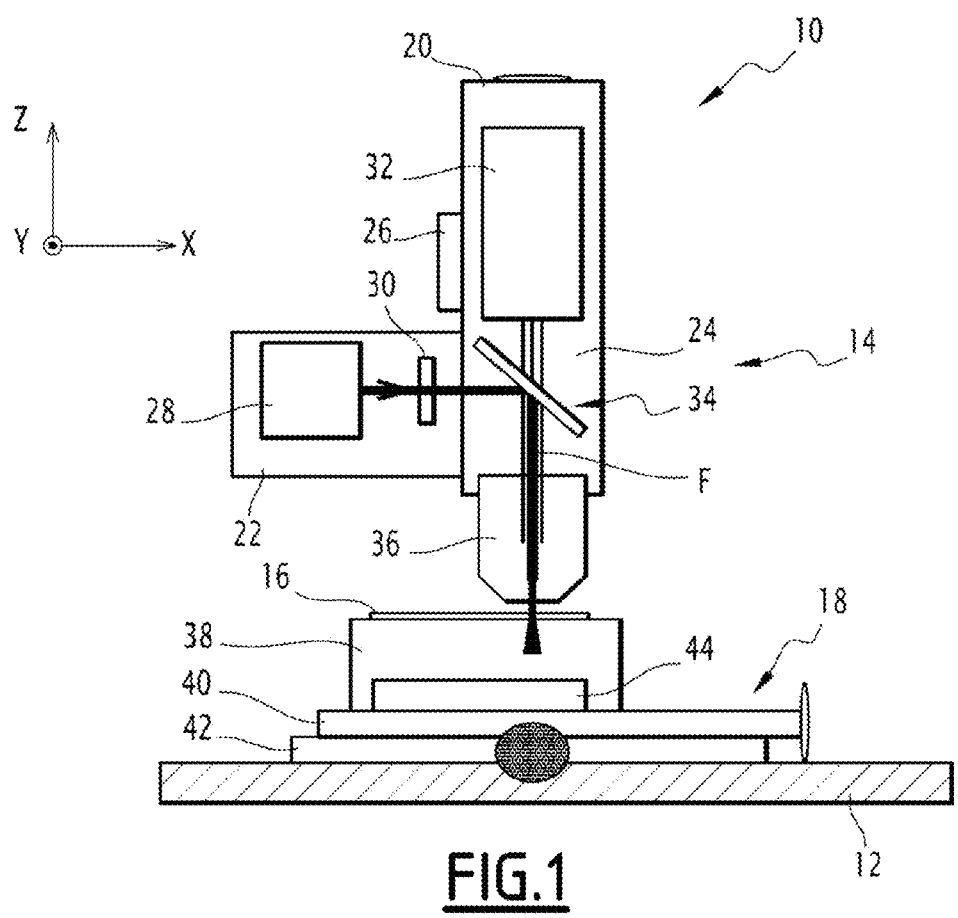
FIG. 1 is a diagram of an exemplary optical system according to a first embodiment of the invention.

The optical system 10 illustrated in FIG. 1 is based on an optical table 12. The optical table 12 is able to ensure good stability to the optical system.

The optical system 10 includes an assembly 14, a sample 16 and a sample holder 18.

The assembly 14 includes a body 20 having the general shape of a T, thereby defining a first branch 22 and a second branch 24. The first branch 22 extends along a direction parallel to the X axis. The X axis belongs to the plane of FIG. 1 and is parallel to the plane of the sample 16. The second branch 24 extends along a direction parallel to the Z axis. The Z axis is an axis perpendicular to the sample 16.

The direction parallel to the X axis is the side direction in the continuation of the description while the direction parallel to the Z axis is the vertical direction. The additional axis orthogonal to both axes X and Z is noted as Y. The direction parallel to the axis Y is called the transverse direction.

The assembly 14 is provided with a vertical translation means 26.

The vertical translation means 26 is able to displace the whole of the body 20 along the vertical direction. The vertical translation means 26 allows modification of the distance between the body 20 and the sample 16.

According to the example of FIG. 1, the vertical translation means is a motor-driven stage.

The first branch 22 of the assembly 14 includes a light source 28 and an attenuation means 30 of the light source 28 in the form of a variable optical density 30.

The light source 28 is able to emit a light beam.

The light source 28 is, according to the example of FIG. 1, a laser source.

For example, the light source 28 is a laser or a light-emitting diode. A light-emitting diode is also designated by the acronym LED for light emitting diode.

Thus, generally, the attenuation means 30 of the light source is positioned so as to reduce the intensity of the incident beam on the sample when it is proceeded with the positioning of the analyte in relation to the light beam. This attenuation means 30 is deactivated when it is proceeded with the analysis of the analyte by means of the analysis device 32. The attenuation means 30 is for example a movable optical density.

The variable optical density 30 gives the possibility of controlling the intensity of the laser beam from the light source 28 at the output of the optical density.

The optical density 30 is movable between a retracted position and a deployed position. When the optical density 30 is in the retraction position, the optical density 30 does not attenuate the beam emitted by the light source 28 while, when the optical density 30 is in the position, the optical density 30 attenuates this beam.

The second branch 24 includes an analysis device 32, a splitter plate 34 and optics 36.

The analysis device 32 is for example capable of conducting an analysis of the Raman spectroscopy type.

When the optical density 30 is in the retracted position, the analysis device 32 comprises an optical probe 37 (not shown) comprising the light source 28, the splitter plate 34 and the focusing optics 36.

The analysis device 32 is then able to analyze the signal emitted by the analyte in response to the beam generated by said optical probe 37.

In other words, when the light source 28 produces an excitation light beam allowing emission of a signal in response from an analyte of the sample 16, said response signal is then analyzed by the analysis device 32.

When the optical density 30 is in the deployed position, the light beam generated by the light source 28 is sufficiently attenuated (typically by a factor comprised between 10 and 1,000) so as to be used as a beam for optimum positioning of the analyte, before the analysis of the latter with the analysis means 32.

The analysis device 32 generally comprises focusing optics (achromatic lens) which allows focusing of the signal emitted by the analyte. The analysis device 32 may be secured to the body 20, or be moved away on the outside of the system 10. In such a case, the signal emitted by the analyte is guided towards the device 32 by means of optical coupling, for example an optical fiber, secured to the body 20. Such an optical coupling means is then considered as being part of the analysis device 32.

The splitting plate 34 is laid out so as to reflect the beam emitted by the light source 28 and to transmit the light collected by the optics 36 to the analysis device 32.

Further, the splitter plate is positioned at 45° of the beam emitted by the light source 28 and at 45° from the transmitted beam. The result of this is that the light beam reflected by the splitter plate is aligned with the beam from the optical probe. 37.

The optics 36 is able to transmit light towards the sample 16 and to collect light from the sample 16.

According to the example of FIG. 1, the optics 36 is a microscope objective.

The sample 16 includes analytes lying on a substrate.

The substrate is a medium for which transmission in the range from 400 nanometers (nm) to 700 nm is greater than or equal to 30%.

For example, the substrate is a glass slide.

As an example, the analytes are microparticles or aggregates of particles of micrometric size. As an example, the particles are organisms or inorganic particles.

The organisms comprise eukaryotic and prokaryotic cells (for example fungi, red corpuscles, white corpuscles or platelets, bacteria or bacterial colonies) and acellular organisms (viruses and prions notably)

Depending on the cases, the cells are isolated or included in organic tissues.

The organisms generally have dimensions of less than or equal to ten microns (μm). Preferably, the organisms considered in the invention have dimensions of less than or equal to 1 μm.

The sample holder 18 includes an imaging device without any lens 38, a side translation means 40 and a transverse translation means 42.

The imaging device without any lens 38 includes a photodetector array 44.

Generally, the term of imaging without any lens designates the formation of an image with a photodetector array placed in front of the analyte, without resorting to magnification optics between the photodetector and the analyte.

The photodetector array 44 is able to establish a diffraction pattern transmitted by the analyte of the sample 16, the diffraction pattern corresponding to the image of the elastically scattered waves by one or several analytes contained in the sample 16. This diffraction image is formed at the photodetector array 44 during illumination of the sample 16 with a beam from the light source 28.

The photodetector array 44 is an image sensor in a plane perpendicular to the vertical axis Z.

The photodetector array 44 is a pixelated image sensor, for example a CMOS (Complementary Metal-Oxide Semiconductor) sensor.

According to an alternative, the photodetector array 44 is a CCD (Charged-Coupled Device) sensor.

The photodetector array 44 additionally includes microlenses, not shown, each microlens being positioned above a corresponding pixel. Such microlenses are integrated into the photodetector array 44. These microlenses give the possibility of improving the collection yield and do not form magnification optics positioned between the sample 16 and the photodetector array 44.

Consequently, the photodetector array 44 is able to form an image of the sample 16, while being placed at a small distance from the sample 16. By small distance, is meant a distance of less than a few centimeters (cm), preferably less than 1 cm, preferentially less than 5 mm and still preferentially 1 mm.

The imaging device without any lens 38 is positioned on the side translation means 40. The side translation means 40 is positioned on the transverse translation means 42.

The side translation means 40 allows variation of the position of the sample holder 18 with respect to the assembly 14 along a direction parallel to the X axis.

The side translation means 40 is a motor-driven stage.

The transverse translation means 42 allows variation of the position of the sample holder 18 with respect to the assembly 14 along a direction parallel to the Y axis.

The transverse translation means 42 is a motor-driven stage.

The side translation means 40 and the transverse translation means 42 are therefore able to modify the position of the sample 16 in a plane which is orthogonal to FIG. 1. Thus, the sample holder 18 may be displaced in a plane orthogonal to the light beam produced by the source 28.

The operation of the optical system 10 will now be described with reference to a method for analyzing the analyte of the sample 16 by means of the light beam F of the analysis probe 37.

The method comprises the regulation of the relative position of the analyte of the sample 16 in relation to the light beam F. An example for regulating this relative position is illustrated subsequently.

The method then includes a step for illuminating the analyte of the sample 16 with a beam from the light source 28.

In this illumination step, the light beam F is attenuated by the attenuation means 30.

The light beam F emitted by the light source 28 is scattered by the analyte of the sample 16.

The imaging device without any lens 38 then takes a transmission image of the beams scattered by the analyte of the sample 16 in order to establish a diffraction pattern noted as FD in the following.

The method comprises a step for modifying the relative position of the analyte of the sample 16 in relation to the light beam F depending at least on one property of the diffraction pattern FD.

The step for modifying the relative position of the sample 16 in relation to the light beam F comprises a step for positioning the analyte in relation to the light beam F, so that the analyte is aligned relatively to the axis of the light beam F. By positioning, it is meant:

an alignment of the analyte of the sample 16 in a plane perpendicular to the light beam F, a modification of the distance between the light source 28 and the analyte of the sample 16 along the axis of propagation of the light beam F.

Generally, the positioning comprises either one of these steps, or their combination.

Generally, the alignment consists of modifying the position of the analyte in relation to the light beam F in a plane perpendicular to the propagation axis, so that the analyte is positioned in the propagation axis of the light beam.

When the distance along the vertical direction Z between the analyte and the assembly 14 is sufficiently large, the light beam F produces a light spot on the image in transmission, in which several diffraction patterns may be distinguished. The centering on the propagation axis then consists of selecting a diffraction pattern of interest in the diffraction pattern FD, corresponding to the analyte which one wishes to analyze, and of placing this diffraction pattern at the centre of said light spot. This is rough centering, based on the position of the diffraction pattern of interest with respect to said light spot. Consequently, the alignment step is based on the use of the next property of the diffraction pattern FD: the position of the diffraction pattern of interest with respect to said light spot.

When the distance along the vertical direction Z between the analyte and the assembly 14 is reduced, in the diffraction pattern FD, the light spot formed by the light beam F corresponds to a diffraction pattern produced by the analyte. It is then proceeded with a fine adjustment of the alignment, based on another criterion of the diffraction pattern FD: the morphology of the diffraction pattern FD. By morphology is meant the shape or the distribution of intensity of the diffraction pattern.

Indeed, a non-symmetrical diffraction pattern FD indicates that the beam F from the light source 28 and the analyte of the sample 16 are not aligned along the side X and transverse Y directions.

In particular, the diffraction pattern FD is not symmetrical when the shape of the diffraction pattern is not symmetrical but also when the distribution of the scatter intensity is not symmetrical.

As an example, let us assume that the observed diffraction pattern FD is an Airy spot with rings having a stronger intensity towards the top of the diffraction pattern FD, which indicates that the sample 16 has to be displaced towards the bottom of the diffraction pattern FD. For an adequate displacement of the sample 16, an Airy spot is then observed with rings having the same intensity in all directions.

The displacement of the analyte of the sample 16 is applied by means of the side translation means 40 and of the transverse translation means 42.

At the end of the step for positioning the analyte of the sample 16, the light beam F of the light source 28 is aligned on the analyte along the directions X and Y.

Preferably, the alignment successively includes rough centering giving the possibility of selecting the analyte of interest and of roughly positioning it, and then fine centering.

Alternatively, the alignment includes only one of both of these centering operations, for example fine centering.

In order to illustrate the application of the step for aligning the analyte of the sample 16, three examples will now be described.

In a first example corresponding to FIG. 2, the analyte is a single bacterium called *Staphylococcus Epidermis*. In the ATCC (acronym for American Type Culture Collection) classification, *Staphylococcus Epidermis* is located by the number 14990. *Staphylococcus Epidermis* has a round shape.

The different FIG. 2, i.e. FIGS. 2A, 2B, 2C, 2D and 2E, represent the diffraction patterns obtained for different positions of the light beam F of the light source 28 with respect to the bacterium. In each of the FIG. 2, the position of the assembly 14 along the vertical direction is set so that only the position of the light beam F of the light source 28 with respect to the bacteria along at least one of the directions X and Y varies.

FIGS. 2A, 2B, 2D and 2E show poor alignment of the light beam F of the light source 28 on the bacterium.

In FIGS. 2A and 2B, it is observed that the presence of interference fringes, the center of which is found on the top left with respect to the center of the spot of the light beam F on the sample 16. This shows that the bacterium is located on the top left with respect to the center of the spot of the light beam F on the sample 16.

In FIGS. 2D and 2E, the presence of interference fringes is observed, the center of which is found on the right with respect to the center of the spot of the light beam F on the sample 16. This shows that the bacterium is located on the right with respect to the center of the spot of the light beam F on the sample 16.

FIG. 2C corresponds to the case when the bacterium is located at the center of the spot of the light beam F on the sample 16. Indeed, interference fringes are observed having a uniform and concentric intensity.

Starting with the case when the bacterium is decentered as observed in FIG. 2A in order to attain the centered case of FIG. 2C, the sample 16 should be displaced along the direction X and/or along the direction Y. In this case, the sample 16 was displaced by 0.4 micrometers towards the right (along the X direction) and by 0.4 micrometers downwards (along the Y direction).

In a second example corresponding to FIG. 3, the analyte is a single bacterium called *Bacillus subtilis*. In the ATCC (acronym for American Type Culture Collection) classification, *Bacillus subtilis* is located by the number 23857. *Bacillus subtilis* has a rod like shape.

The various FIG. 3, i.e. FIGS. 3A, 3B, 3C, 3D, 3E and 3F represent diffraction patterns obtained for different positions of the light beam F from the light source 28 with respect to the bacterium. In each of the FIG. 3, the position of the assembly 14 along the vertical direction is set so that only the position of the light beam F from the light source 28 with respect to the bacterium along at least one of the directions X and Y varies.

For reasons similar to the explained reasons for FIGS. 2A, 2B, 2D and 2E, FIGS. 3A, 3B, 3C, 3E and 3F show poor alignment of the light beam F from the light source 28 on the bacterium. Indeed, the observed interference fringes do not have uniform intensity and are not perfectly concentric.

On the contrary, FIG. 3D corresponds to the case when the bacterium is located at the center of the spot of the light beam F on the sample 16. Indeed, interference fringes are observed having a uniform and concentric intensity.

In this second example, in order to pass from the configuration in which the bacterium is decentered as observed in FIG. 3A in order to reach the centered configuration of FIG. 3D, the sample 16 was displaced by 0.8 micrometer towards the right (along the X direction). In this second example, the sample 16 was not displaced along the Y direction.

Figure 4:
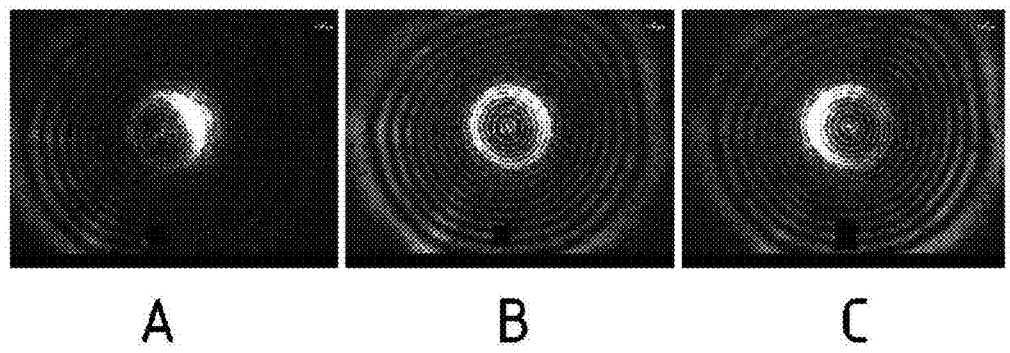
FIGS. 4A to 4C are diffraction patterns observed during a third embodiment of a step of an alignment method according to the invention.

In a third example corresponding to FIG. 4, the analyte is a bacterial microcolony obtained by the growth of *Escherichia coli* bacteria. In the ATCC (acronym for American Type Culture Collection) classification, *Escherichia coli* is located by the number 23857. The *Escherichia coli* bacteria were cultivated on a gelose nutrient medium for 6 hours. The obtained diameter for the microcolony is 150 microns.

The various FIG. 4, i.e. FIGS. 4A, 4B and 4C represent diffraction patterns obtained for different positions of the light beam F from the light source 28 with respect to the bacterium. In each of FIG. 4, the position of the assembly 14 along the vertical direction is set so that only the position of the light beam F from the light source 28 with respect to the bacterium along at least one of the directions X and Y varies.

In the third example, the light beam F from the light source 28 is considered as centered on the microcolony when the pattern illustrated in FIG. 4B is obtained. Indeed, the intensity of the observed diffraction rings is distributed symmetrically. By contrast, FIGS. 4A and 4C correspond to decentered configurations.

In this second example, in order to pass from the configuration in which the colony is decentered as observed in FIG. 4A in order to reach the centered configuration of FIG. 4B, the sample 16 was displaced by 11 micrometers to the right (along the X direction). In this second example, the sample 16 was not displaced along the Y direction. Alignment implies displacement, along the vertical direction, of the assembly 14 by using the vertical translation means 16, so as to centre the analyte of interest in relation to the light beam.

The alignment and the modification of the distance between the light source 28 and the analyte of the sample 16 along the propagation axis of the light beam F are thus ensured concomitantly so that at the end of the positioning, the positioning of the diffraction pattern of interest is centered with respect to said light spot on the diffraction pattern FD.

Further, the alignment is notably achieved in an iterative way, by modifying the rough centering in the plane perpendicular to the beam at each iteration.

According to the type of conducted analysis, it is also useful to adjust the distance between the sample 16 and the support 14, so that the size of the light beam F, produced by the light source 28, coincides with the size of the analyte, or is smaller than the latter. Indeed, the section of the light beam F at the plane of the sample 16 varies according to the distance between the objective 36 and the sample 16. By adjusting this section to the dimensions of the analyte, or even to a smaller dimension, illumination of the vicinity of the analyte is avoided. The emission of a parasitic signal, non-specific to the analyte is then avoided.

This adjustment of the size of the light beam F with respect to the analyte is obtained by the step for modifying the relative position of the analyte of the sample 16 in relation to the light beam F.

In this case, the step for modifying the relative position also comprises a step for modifying the distance between the analyte and the assembly 14, along the vertical direction Z, until the observed analyte occults the light beam F from the light source 28, i.e. when it is not possible to identify a diffraction pattern but a diffuse spot, and when this spot has a minimum light intensity in its centre.

Thus, the imaging device without any lens 38 allows adjustment of the size of the light beam F in the plane of the sample 16.

This adjustment of the size of the light beam F with respect to the analyte may be completed by applying a step for modifying the relative position of the analyte of the sample 16 in relation to the light beam F in order to maximize the radiation emitted by the analyte of the sample 16 in response to excitation of the light beam F.

The method also comprises stopping of the attenuation of the light beam F in order to generate an excitation of the light beam F of larger amplitude.

The method then includes a step for acquiring an analysis signal resulting from the radiation emitted by the analyte of the sample 16 in response to the illumination by the light beam F by the analysis device 32, the light source 28 then not being attenuated by the attenuation means 30.

The observation of the signal produced by the analysis device 32 allows modification of the distance between the analyte and the device 14 in order to at least optimize a characteristic of the acquired analysis signal.

This characteristic is for example an intensity, a signal-to-noise ratio or a spectral resolution.

At the end of this step, the relative position of the analyte of the sample 16 in relation to the light beam F is regulated.

The method then comprises an analysis step by the analysis device 32 of the radiation emitted by the analyte of the sample 16 in response to the illumination with the light beam F.

An example for applying an analysis method of the analyte of the sample 16 by means of the light beam F of a Raman probe 37 is illustrated by the experiment shown with reference to FIGS. 5 to 22.

The images of FIGS. 5 to 21 are images of a diffraction pattern from the photodetector array 44. Each FIGS. 5 to 21 corresponds to a vertical distance between the assembly 14 and the sample 16.

In the shown experiment, the sample holder 16 includes a single bacterium called *Bacillus Cereus*.

Figure 13:
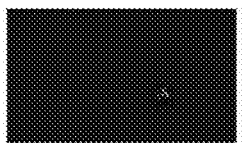
Figure 19:
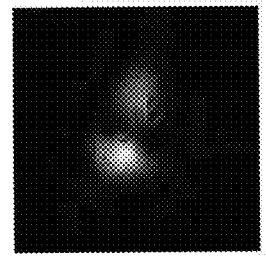

FIG. 19 corresponds to the reference distance of 23 mm between the assembly 14 and the sample 16 since FIG. 19 corresponds to the maximum Raman signal observed in FIG. 13.

Figure 5:
FIGS. 5 to 21 are diffraction patterns observed when an alignment method according to the invention is applied.
Figure 6:
Figure 7:
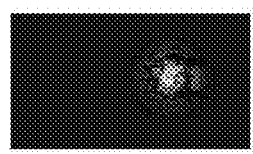
Figure 8:
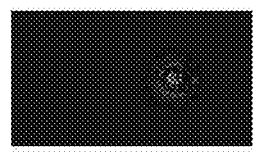
Figure 9:
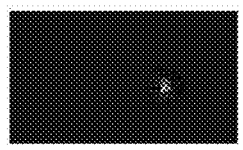
Figure 10:
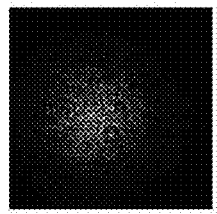
Figure 11:
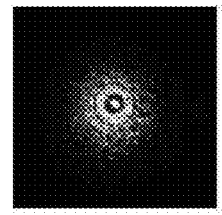
Figure 12:
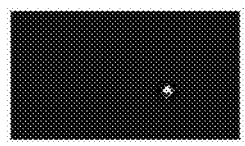
Figure 14:
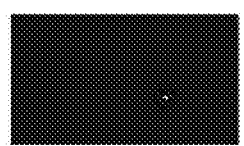
Figure 15:
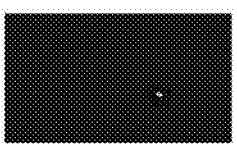
Figure 16:
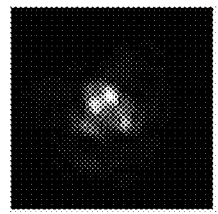
Figure 17:
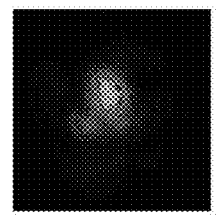
Figure 18:
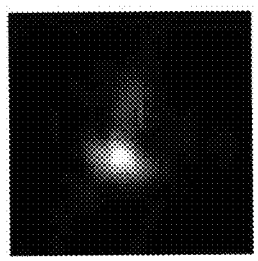
Figure 20:
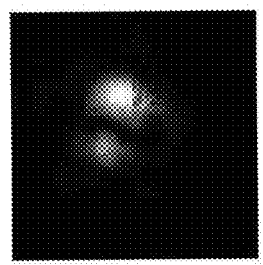
Figure 21:
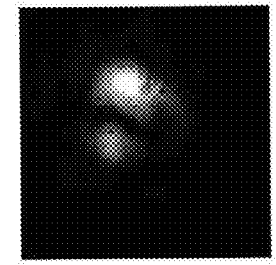

Respectively, FIG. 5 corresponds to a vertical distance between the assembly 14 and the sample 16 of more than 43.922 millimeters (mm) with respect to the reference distance; FIG. 6 to a distance greater than 10.922 mm; FIG. 7 to a distance greater than 3.222 mm; FIG. 8 to a distance greater than 2.122 mm; FIG. 9 to a distance greater than 1.022 mm; FIG. 10 to a distance greater than 722 µm; FIG. 11 to a distance greater than 252 µm; FIG. 12 to a distance greater than 162 µm; FIG. 13 to a distance greater than 77 µm; FIG. 14 to a distance greater than 56 µm; FIG. 15 to a distance greater than 45 µm; FIG. 16 to a distance greater than 30 µm; FIG. 17 to a distance greater than 21 µm; FIG. 18 to a distance greater than 2.6 µm; FIG. 20 to a distance of less than 5.0 µm and FIG. 21 to a distance of less than 10.3 µm.

In FIGS. 5 to 12, the diffraction pattern obtained on the imaging device without any lens 38 gives the possibility of observing several analytes of the sample 16. The observation of the sample 16 by means of the imaging device without any lens 38 then gives the possibility of having a global view, including different analytes.

When the distance is less than 252 µm with respect to the reference distance, the diffraction pattern of a single analyte is observed on the imaging device without any lens 38.

Thus, modification of the position of the sample 16 with respect to the support 14 gives the possibility of selecting an analyte of interest and of aligning the latter with respect to the axis of the light beam F.

FIGS. 5 to 12 illustrate consequently the rough centering as described earlier.

In FIGS. 13 to 17, it is successively observed from the largest vertical distance down to the smallest vertical distance that the size of the region illuminated by the laser decreases from a size greater than that of the bacterium until it is equal to that of the bacterium (case of FIG. 17, when the beam is occulted by the bacterium).

The laser beam and the bacterium are then aligned along the direction Z.

In the particular case of this Raman analysis, optimum adjustment is achieved, from the position in which the diffraction pattern is occulted, by adjusting the distance along the vertical direction between the assembly 14 and the analyte depending on the observed Raman spectrum. More specifically, the optimum distance along the vertical direction corresponds to that for which the peaks, in the relevant area of interest, are the most resolved and the most intense. FIGS. 18 to 21 illustrate this adjustment based on the analysis signal.

In the example illustrated in FIGS. 18 to 21, the analysis device 32 is a Raman spectrometer. The adjustment of the distance is of the order of a few microns. The vertical distance is then adjusted according to the Raman spectrum, so as to detect more peaks in the spectral region of interest corresponding to the signals emitted by bacteria (i.e. a shift comprised between 1,000 and 1,700 cm$^{-1}$). The optimum value is that of FIG. 19 (or FIG. 18): indeed, for these figures, the Raman spectrum includes more sufficiently resolved peaks in the area of interest. Moreover, the parasitic signal from the vicinity of the bacterium is significantly reduced: the measurement is therefore more specific to the analyte of interest.

Figure 22:
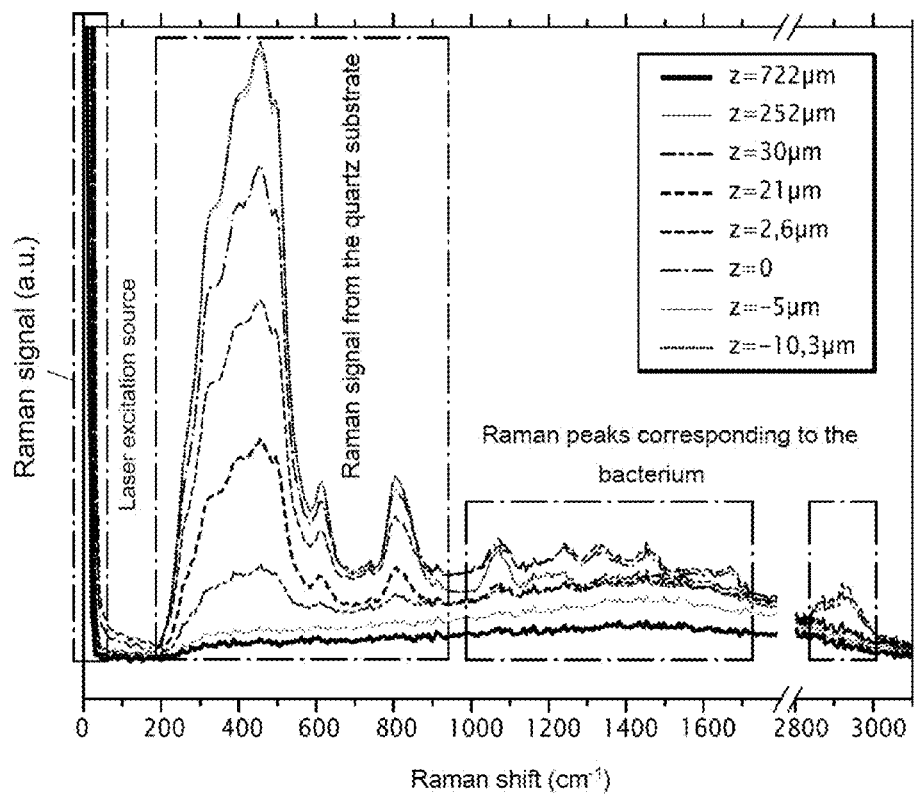
FIG. 22 is a graph showing the recorded Raman spectra corresponding to FIGS. 5 to 21.

The spectra obtained in the different positions of FIGS. 10, 11, 16 to 21 are illustrated in FIG. 22. As announced, if the range of wavelengths comprised between 200 cm$^{-1}$ and 925 cm$^{-1}$ is not considered since it corresponds to a spectral signature of the quartz of the sample 16, it is observed that in the ranges of wavelengths respectively comprised between 1,000 cm$^{-1}$ and 1,700 cm$^{-1}$ and 2,850 cm$^{-1}$ and 3,000 cm$^{-1}$, the Raman signal corresponding to FIG. 19 (or FIG. 18) is the largest amplitude signal.

The method therefore actually gives the possibility of obtaining an alignment of the probe on the analyte to be observed.

Figure 23:
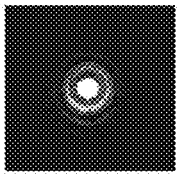
FIG. 23 is a table associating a plurality of diffraction patterns respectively with the species of an observed analyte and with an image-taking position in the method according to the invention.

The experiment described was reproduced successfully on several different bacteria, notably *Escherichia Coli* and *Bacillus Subtilis*, and on cells and *Staphylococcus Epidermis* SE9 (see FIG. 23).

The proposed alignment method does not imply a step for changing a collection objective. There results a gain in time and simplification of the optical system 10 to be used both instrumentally and on a software level.

The method gives the possibility of using the same light source 28 for the positioning (i.e. alignment of the analyte on the beam F and adjustment of the size of the beam F on the plane of the sample 16) of the analyte and for its analysis without any use of optics positioned outside the assembly 14.

The alignment is advantageously achieved when the light source 28 is attenuated, for example by means of an optical density 30, the analysis then being carried out without any attenuation.

This guarantees proper alignment of the beam from the light source 28 and from the probe without involving any verification of the alignment of the optional optics. The result of this is an improvement in the robustness of the optical system 10. The optical system 10 may therefore be used in systems which may be transported in the field.

The method shown may be easily automated by means of software processing and by using server-control of the translation means 26, 40, 42.

In this method, the probe beam from the light source 28 and the analysis device 32 move together during the vertical alignment step while the sample 16 is fixed. As compared with conventional systems in which it is the sample 16 for which the position is modified along the vertical direction, a step for realignment of the beam along the side X and transverse Y directions is thus avoided for each new position of the sample along the vertical direction Z.

According to an alternative, the diffraction pattern FD obtained with the photodetector array 44 is also used for performing a pre-classification of the analyte contained in the sample 16.

The diffraction pattern actually gives the possibility of accessing the size, the shape of the analyte.

This piece of information notably allows identification of the analyte.

FIG. 23 associates in a table a plurality of diffraction patterns respectively with an observed analyte and with a vertical distance between the light source 28 and the sample 16 corresponding to the distance for taking the image with the imaging device 38.

The first species is a *Bacillus Cereus*, the second species a *Bacillus Subtilis* and the third species an *Escherichia Coli*.

In the table of FIG. 23, with each species are associated three diffraction patterns taken from three different distances (position 1, position 2 and position 3).

It is actually observed that the shapes of the diffraction patterns are different according to the relevant analyte, which gives the possibility of identifying the analyte from observation of the diffraction pattern.

The method is applied for any type of analysis device 32. As an example, the optical system 10 shown with reference to FIG. 1 may also be used with other imaging devices such as reflective diffraction, fluorescence or self-fluorescence.

Figure 24:
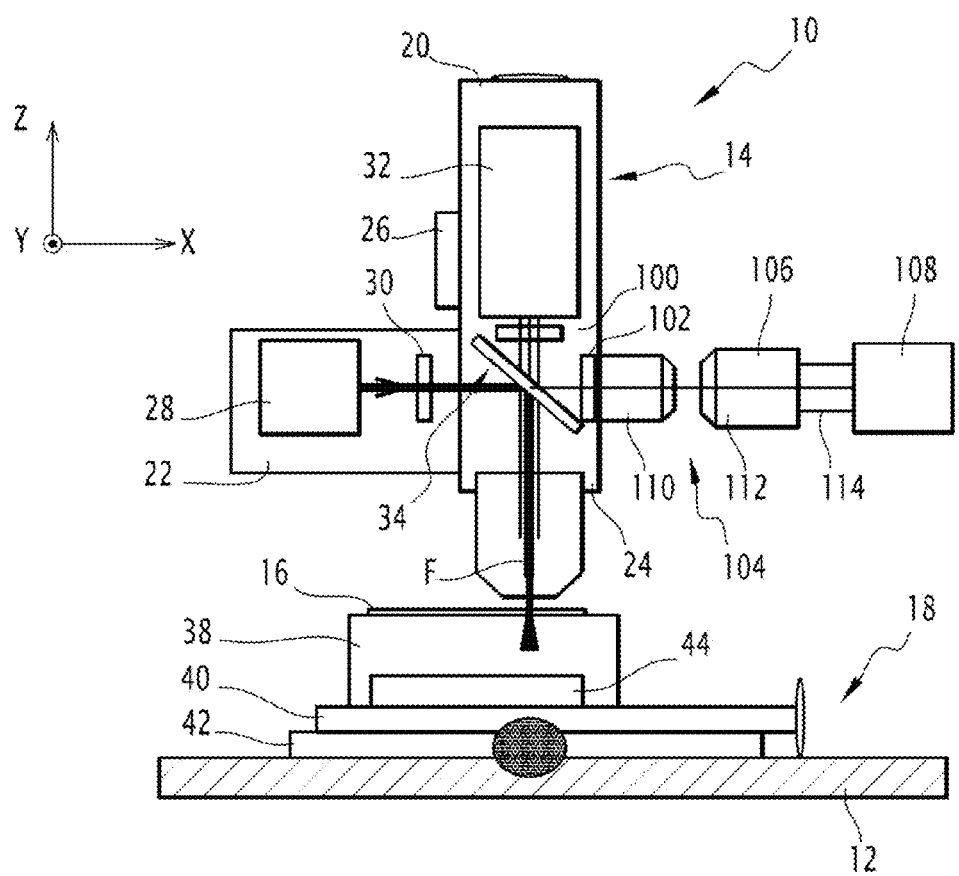
FIG. 24 is a schematic view of an exemplary optical system according to a second embodiment of the invention.

A second embodiment of the optical system is also shown in FIG. 24.

The optical system 10 includes the same elements as the optical system of FIG. 1.

The optical system 10 also includes a mirror 100 positioned between the analysis device 32 and the splitter plate 34.

The mirror 100 is a planar mirror.

The mirror 100 is movable between a first position in which it reflects the beam transmitted by the splitter plate 34 and a second position in which it does not interact with the transmitted beam.

The optical system 10 also includes a fluorescence filter 102 able to filter a light beam.

The filter 102 is positioned so as to filter a beam reflected by the mirror 100 and the splitter plate 34 when the mirror 100 is in the first position.

The optical system 10 also includes an imaging device with a lens 104.

According to the example of FIG. 24, the imaging device with the lens 104 comprises magnification optics 106 and a camera 108.

The magnification optics 106 comprises a first microscope objective 110 mounted on the assembly 14 and a second microscope objective 112 mounted on the camera 108 by means of an extender ring 114.

The magnification optics 106 is able to obtain magnification of the beam and to focus it on the photodetectors of the camera 108.

In this embodiment, the optical system 10 is used for producing imagings with fluorescence.

In the absence of the filter 102, the optical system 10 is used for performing diffraction reflective imagings.

In the absence of a filter 102 and by illuminating with white light the sample 16, the optical system 10 is both used for performing imagings by reflective diffraction, and for performing white light imagings in direct space.

This optical system 10 also allows the application of the alignment method proposed for the first embodiment of the optical system 10.

Consequently, in the proposed embodiment, it is possible to perform a single alignment in order to conduct two successive different analyses on the sample 16.

Further, although the different embodiments have been presented with reference to an imaging device 38 without any lenses, the method may also be applied with an imaging device 38 with lenses provided that the latter allows observations in Fourier space. Indeed, according to the invention, alignment of an analyte is proposed by using properties observed in Fourier space and not in direct space as this is the case in the state of the art. The regulation method which results from this is faster to apply than the regulation methods of the state of the art.

The invention claimed is:

1. A method for regulating the relative position of an analyte of a sample (16) in relation to a light beam wherein the method comprises:
   illuminating the analyte of the sample with the light beam,
   taking with the imaging device a transmission image of the beams scattered by the analyte of the sample for establishing a diffraction pattern, and
   modifying the relative position of the analyte of the sample in relation to the light beam according to at least one property of the diffraction pattern,
   wherein the taking with an imaging device of a transmission image of the beams scattered by the analyte of the sample for establishing a diffraction pattern and the modification of the relative position of the analyte of the sample in relation to the light beam according to at least one property of the diffraction pattern are carried out several times.

2. The regulation method according to claim 1, wherein the light beam stems from a light source and propagates along an axis of propagation and wherein the modification of the position of the analyte of the sample in relation to the light beam comprises at least one of the group consisting of:
   a step of aligning the analyte of the sample on the axis of propagation of the light beam,
   a step of modifying the distance between the light source and the analyte of the sample along the axis of propagation so that the diffraction pattern resulting from the beams diffracted by the analyte of the sample is at the center of the diffraction pattern,
   a step of adjusting the distance between the light source and the analyte of the sample along the axis of propagation until the analyte of the sample occults the light beam, and
   a step of modifying the relative position of the analyte of the sample in relation to the beam for maximizing the radiation emitted by the analyte of the sample in response to the excitation of a light beam from the light source.

3. The regulation method according to claim 1, wherein the light beam stems from a light source and propagates along an axis of propagation and wherein the modification of the position of the analyte of the sample in relation to the light beam comprises at least two of the group consisting of:
   a step of aligning the analyte of the sample on the axis of propagation of the light beam,
   a step of modifying the distance between the light source and the analyte of the sample along the axis of propagation so that the diffraction pattern resulting from the beams diffracted by the analyte of the sample is at the center of the diffraction pattern,
   a step of adjusting the distance between the light source and the analyte of the sample along the axis of propagation until the analyte of the sample occults the light beam, and
   a step of modifying the relative position of the analyte of the sample in relation to the beam for maximizing the radiation emitted by the analyte of the sample in response to the excitation of a light beam from the light source.

4. The regulation method according to claim 1, wherein the light beam forms a spot in the transmission image and the property is the morphology of the diffraction pattern or the position of the diffraction pattern with respect to the spot formed by the light beam in the transmission image.

5. The regulation method according to claim 1, wherein the method further comprises:
   the acquisition of an analysis signal resulting from the radiation emitted by the analyte of the sample in response to the illumination with the light beam by an analysis device, and
   modifying the relative position of the analyte of the sample in relation to the beam in order to optimize at least one characteristic of the acquired analysis signal.

6. The regulation method according to claim 1, wherein the imaging device is an imaging device without any lenses.

7. A method for analyzing an analyte of a sample by means of a light beam wherein the method comprises:
   regulating the relative position of the analyte of the sample in relation to the light beam by applying a regulation method according to claim 1, and
   analyzing with a device for analyzing the radiation emitted by the analyte of the sample in response to the illumination by the light beam,
   wherein the method successively comprises:
   attenuating the light beam with an attenuation means,
   regulating the relative position of the analyte of the sample in relation to the light beam,
   stopping the attenuation of the light beam, and
   analyzing with the analysis device.

8. The analysis method according to claim 7, wherein the method further comprises:
   determining characteristics of the analyte of the sample from the diffraction pattern established by the imaging device.

9. The regulation method according to claim 1,
   wherein the light beam stems from a light source propagates along an axis of propagation,
   wherein at a first step of taking, a first transmission image is taken and a first diffraction pattern is established, the first transmission image comprising a light spot formed by the light beam and at a first step of modifying, the property is the position of the first diffraction pattern with relation to the light spot, and
   wherein at a second step of taking, a second transmission image is taken and a second diffraction pattern is established, and at a second step of modifying, the property is the morphology of the second diffraction pattern.

10. The regulation method according to claim 9, wherein the method further comprises a step of adjusting the distance between the light source and the analyte of the sample along the axis of propagation until the analyte of the sample occults the light beam, the step of adjusting being carried out after the second step of modifying.

11. The regulation method according to claim 9, wherein the method comprises the attenuating the light beam with an attenuation means before the first step of taking, and after the second step of modifying, the method comprises:
   stopping the attenuation of the light beam so as to obtain an excitation beam,
   exciting the analyte of the sample with the excitation beam,
   modifying the relative position of the analyte of the sample in relation to the beam for maximizing the radiation emitted by the analyte of the sample in response to the excitation of the excitation beam.

* * * * *